United States Patent
Bosch et al.

(10) Patent No.: US 6,504,017 B1
(45) Date of Patent: Jan. 7, 2003

(54) ERTHROMYCIN A OXIME SOLVATES

(75) Inventors: Immaculada Bosch, Vic/Barcelona (ES); Victor Centellas, Cardedeu/Barcelona (ES); José Diago, Granollers/Barcelona (ES)

(73) Assignee: Biochemie S.A., Granollers/Barcelona (ES)

( * ) Notice: Subject to any disclaimer, the term of this patent is extended or adjusted under 35 U.S.C. 154(b) by 0 days.

(21) Appl. No.: 09/462,302

(22) PCT Filed: Jul. 6, 1998

(86) PCT No.: PCT/EP98/04166

§ 371 (c)(1),
(2), (4) Date: Jan. 4, 2000

(87) PCT Pub. No.: WO99/02541

PCT Pub. Date: Jan. 21, 1999

(30) Foreign Application Priority Data

Jul. 8, 1997 (GB) .............................................. 9714358
May 13, 1998 (GB) .............................................. 9810245

(51) Int. Cl.$^7$ .............................................. C07H 17/08
(52) U.S. Cl. ...................................................... 536/7.4
(58) Field of Search ................................ 536/7.4, 18.5; 514/29

(56) References Cited

U.S. PATENT DOCUMENTS 3,478,014 A * 11/1969 Slobodan et al. ........... 260/210

FOREIGN PATENT DOCUMENTS

| EP | 0 342 990 A | * | 11/1989 |
| EP | 0 503 949 A | * | 9/1992 |
| WO | 97 38000 A | * | 10/1997 |

* cited by examiner

*Primary Examiner*—Elli Peselev
(74) *Attorney, Agent, or Firm*—Hesna J. Pfeiffer

(57) ABSTRACT

Erythromycin A oxime in the form of a hemihydrate.

1 Claim, No Drawings

# ERTHROMYCIN A OXIME SOLVATES

The present invention relates to the synthesis of antibacterial macrolides, such as of the erythromycin, for example erythromycin A, type, e.g. roxithromycin, dirithromycin, clarithromycin, azithromycin and similar compounds.

A compound useful in the production of antibacterial macrolides, such as of the erythromycin type is, e.g. described in U.S. Pat. No. 3,478,014, namely a compound of formula

I hereinafter designated as erythromycin A oxime. Erythomycin A is a well known, e.g. antibacterial agent. Isolated erythromycin A oxime, e.g. in free-base form obtained according to known processes may be obtained in unstable form, e.g. it may be hygroscopic. We have now found erythromycin A oxime in free-base form in stable, e.g. non hygroscopic form, e.g. a compound according to the present invention may keep a constant water content under normal, e.g. normal air humidity, environmental conditions for at least 24 hours.

In one aspect, the present invention provides a compound of formula I
  in anhydrous and stable form, or
  in the form of a solvate with non-halogenated organic solvent; or
  in the form of a hemihydrate.

Non-halogenated organic solvent as used herein is able to form a solvate with a compound of formula I and is able to form a two-phase system with water. Non-halogenated solvent includes e.g. acetic acid alkyl esters, preferably with alkyl of more than 1 C-atom, e.g. $C_{2-8}$, such as $C_{2-6}$, such as ethyl, propyl and butyl acetates, e.g. isopropyl acetate and n-butylacetate; and alkyl ketones, e.g. dialkyl ketones, e.g. methyl-butyl ketones, such as methyl-isobutylketone. Mixtures of individual solvents, e.g. as described above are included. Non-halogenated organic solvent as used herein means that the chemical formula of that organic solvent does not contain halogen atoms. In contrast to that a halogenated organic solvent means that the chemical formula thereof contains at least one halogen atom. If not otherwise defined herein alkyl includes $(C_{1-12})$alkyl, e.g. $(C_{1-8})$alkyl, such as $(C_{1-6})$alkyl, e.g. $(C_{1-4})$alkyl. In erythromycin A oxime, e.g. of formula I, in the form of a hemihydrate, according to the present invention there may be determined
  a water content (Karl Fischer) of about 1.6% (theory: 1.19%; monohydrate: 2.35%) which may remain below 2.35%, e.g. 2%, e.g. after several, e.g. 24 hours and more, e.g. several days, under normal, e.g normal air humidity, environmental conditions an endotherm at 136° C. in differential scanning calorimetry (heating rate 10° C./min)
  a loss of 1.15% of weight between 100° C. and 200° C. in thermal gravimetric analysis (theory:1.19%)
  a high content of the E isomer and a low content of the Z isomer.

A compound of the present invention including e.g. a compound of formula I in anhydrous and stable form, and a compound of formula I in the form of a solvate with non-halogenated solvent and a compound of formula I in the form of a hemihydrate may be obtained as follows:

Erythromycin A oxime, e.g. of formula I
  may be treated in a mixture of water and aromatic solvent; or,
  may be extracted I into a non-halogenated solvent which is able to form a solvate with a compound of formula I and which is able to form a two phase system with water;
and a compound of the present invention may be isolated; and
an isolated compound of the present invention treated with aromatic solvent may be dried at temperatures at 50° C. or above.

In another aspect the present invention provides a process for the production of a compound of formula I in the form of a solvate, comprising
  treating a compound of formula I in a mixture of water and aromatic solvent and isolating a compound of formula I in the form of a hemihydrate; or
  extracting a compound of formula I, into non-halogenated solvent and isolating a compound of formula I in the form of a solvate with non-halogenated organic solvent; and
a process for the production of a compound of formula I in anhydrous and stable form, comprising drying a compound of formula I in the form of a solvate with non-halogenated solvent at temperatures of 50° C. or above.

In the process of the present invention a compound of formula I in free base form, or in the form of a salt, e.g. a hydrochloride, and/or in the form of a solvate, such as a hydrate, preferably in the form of a salt may be brought into contact with a mixture containing water and an aromatic solvent in the production of a hemihydrate of formula I, or in non-halogenated solvent, e.g. as defined above for the production of a compound of formula I in the form of a solvate with non-halogenated solvent; e.g. a compound of formula I may be dissolved or suspended in a mixture containing water and an aromatic solvent or non-halogenated solvent. The pH of a mixture obtained may be at an pH where a compound of formula I is present in free base form, including e.g. a pH of 7.5 to 10.5, for example 9.0 to 10.0. Adjustment of the pH to e.g. 7.5 to 10, e.g. if a compound of formula I is in the form of a salt, may be carried out e.g. by use of an appropriate base, e.g. addition to a suspension or a solution of a compound of formula I in a solvent. An appropriate base includes a base which is able to set free a compound of formula I in the form of a salt; including, for example, an inorganic base, such as an alkali-, e.g. sodium-, potassium-; earth alkali-, e.g. calcium-, magnesium-; and ammonium-; -hydroxide, -carbonate, -bicarbonate; and an organic base, such as ammonia and an amine, e.g. alkyl amine, such as triethylamine or diisopropylamine. A base may be preferably a hydroxide, e.g. sodium and ammonia; preferably in aqueous solution; e.g. in about 10% to 35%, such as 15% to 30% aqueous solution. The base may, e.g. be combined with a solution or suspension of a compound of formula I in salt form in water, e.g. in mixture with an aromatic or non-halogenated solvent.

An aromatic solvent as used herein includes aromatic organic solvent such as benzene, toluene, xylene, e.g. o-xylene, m-xylene, p-xylene; preferably toluene or xylene; and an aromatic solvent system, e.g. mixtures of individual aromatic solvent, e.g. as described above; preferably a mixture of o-xylene and/or m-xylene and/or p-xylene; and a mixture of aromatic solvent with one or more other organic solvents, e.g. organic solvent which may be useful in organic chemistry. Preferably in the suspension or solution of a compound of formula I the non-halogenated solvent is present without any further non-halogenated organic solvent; optionally one or more, e.g. non-halogenated organic solvents miscible or immiscible with water may be present; provided that a two phase system with water is formed in a mixture of solvents; and provided that a compound of formula I in free base form is obtained from the mixture in the form of a solvate with non-halogenated solvent. Preferably the aromatic solvent is present without any further organic solvent; optionally an organic solvent, e.g. such as an organic solvent useful in organic chemistry, preferably a solvent the chemical formula of which does not contain a halogen atom, may be present; provided that a compound of formula I in free base form is obtained in the form of a hemihydrate after combination with a base; e.g. in an isolation step. The non-halogenated solvent may be used in an amount sufficient to dissolve a compound of formula I, e.g. during an extraction of a compound of formula I into the organic phase which may be dependent on the solubilizing characteristics of the solvent. Per gram of a compound of formula I, e.g. 2 ml to 20 ml and more, for example 3 ml to 15 ml, such as 5 to 12 ml of the non-halogenated organic solvent may be used. The amount of non-halogenated organic solvent in respect with the amount of water may be dependent on the chemical nature of the organic solvent and on the miscibility characteristics of the organic solvent with water. The range of water and non-halogenated organic solvent used may be such that a two phase system is formed. The appropriate amount of water and the amount of non-halogenated organic solvent can be easily determined. The amount of aromatic solvent is not critical and includes a range of, e.g. ca., 0.5 ml, such as 3 ml, to 20 ml per gram of a compound of formula I; the amount of water in case of use of aromatic solvent is not critical and include a range from traces of water in an aromatic solvent, e.g. which may be sufficient to form a hemihydrate of erythrymcin A oxime, to an amount of water which causes formation of a two phase system with an aromatic solvent; or even higher amounts of water, such as from 0.1 to 100 parts (v/v) of water per part (v/v) of aromatic solvent; e.g. 0.5 to 10 parts (v/v).

The temperature in a mixture of a compound of formula I with water and aromatic or non-halogenated solvent may be below, about at, or above room temperature; such as from about 0° C. to about 60° C., eg. from 0° C. to 60° C; such as from 10° C. to 50° C.; e.g. 20° C. to 50° C. in case of use of aromatic solvent; and, e.g. room temperature in case of use of non-halogenated solvent. Erythromycin A oxime in the form of a salt, e.g. a hydrochloride, e.g. as useful as a starting material in a process of the present invention is known and may be obtained by a process as conventional. A mixture of erythromycin A oxime, water and aromatic or non-halogenated solvent obtainable according to the present invention may be stirred, e.g. in order to achieve a uniform mixture.

In case of use of non-halogenated organic solvent and production of a solvate of a compound of formula I with non-halogenated solvent a compound of formula I may be extracted into the organic phase; the organic phase may be separated off from the aqueous phase, e.g. as conventional and optionally dried, e.g. as conventional, for example by addition of a drying agent such as sodium sulphate, e.g. anhydrous, and the solvent may be, e.g. partially, removed; for example by distillation, e.g. under reduced pressure. Precipitation of a compound of formula I in the form of a solvate with non-halogenated solvent may occur and the precipitate may be isolated as usual, e.g. by filtration. A highly pure solid compound of formula I in form of a solvate having a low content of Z-isomer may be obtained, e.g. in stable, e.g. non-hygroscopic form. A compound of formula I in form of a solvate with non-halogenated organic solvent according to the present invention may be a true solvate composed of about one solvent molecule per molecule of a compound of formula I and may be anhydrous and stable under normal environmental, e.g. normal air humidity conditions. A solvate of the present invention provides an intermediate in surprisingly high purity, e.g. having a low Z-isomer content, such as below 2%, and is useful, e.g. as such, in reactions of a compound of formula I. The water content may be below 1%, even below 0.3%, such as 0.2 to 0.9%, e.g. 0.3 to 0.6%, and the solvate may be non-hygroscopic. A compound of formula I in form of a solvate with non-halogenated organic solvent according to the present invention may be stable and may be dried, e.g. in vacuo, e.g. at temperatures up to below 50° C., e.g. from 20° C. to about 45° C. A drying temperature range for an isosopropyl acetate solvate of 20° C. to 35° C. and for an n-butyl acetate and methyl isobutyl ketone solvate of 30° C. to 45° C. in vacuo is preferred. If a solvate according to the present invention is dried, e.g. at temperatures from 50° C. and above, e.g. in vacuo, for example at about temperatures in vacuo of 50° C. to 90° C., such as 60° C. to 80°, e.g. for an isosopropyl acetate solvate of 65° C. to 75° C. and for an n-butyl acetate and methyl isobutyl ketone solvate of 50° C. to 70° C., a compound of formula I, e.g. in non-solvate form, in surprisingly stable, e.g. non-hygroscopic, and anhydrous form may be obtained.

A compound of formula I in stable and anhydrous form is new and may show a X-ray powder diffraction pattern, e.g. dependent on the type of solvate dried to obtain the compound of formula I in stable and anhydrous form: The X-ray powder diffraction pattern may be substantially as shown below in Tables 1 and 1a (Table 1a is more detailed than Table 1), if an isopropyl acetate solvate is dried;

Tables 2 and 2a, (Table 2a is more detailed than Table 2) if an n-butylacetate solvate is dried; and Tables 3 and 3a, (Table 3a is more detailed than Table 3) if an methyl-isobutylketone solvate is dried:

TABLE 1

| d(Å) | $I/I_0$ |
|---|---|
| 12.98 | 1.00 |
| 8.58 | 0.34 |
| 8.31 | 0.69 |
| 6.76 | 0.39 |
| 6.57 | 0.37 |
| 5.64 | 0.36 |
| 4.40 | 0.37 |

TABLE 1a

| d(Å) | $I/I_0$ |
|---|---|
| 15.18 | 0.26 |
| 12.98 | 1.00 |
| 10.16 | 0.30 |
| 8.58 | 0.34 |
| 8.31 | 0.69 |
| 7.53 | 0.22 |
| 6.76 | 0.39 |

TABLE 1a-continued

| d(Å) | I/I₀ |
|---|---|
| 6.57 | 0.37 |
| 5.64 | 0.36 |
| 5.23 | 0.21 |
| 5.16 | 0.27 |
| 4.81 | 0.25 |
| 4.40 | 0.37 |

TABLE 2

| d(Å) | I/I₀ |
|---|---|
| 11.72 | 0.71 |
| 11.00 | 0.48 |
| 6.27 | 0.94 |
| 5.90 | 0.68 |
| 5.75 | 0.54 |
| 5.46 | 0.49 |

TABLE 2a

| d(Å) | I/I₀ |
|---|---|
| 18.90 | 0.36 |
| 12.64 | 0.40 |
| 11.72 | 0.71 |
| 11.00 | 0.48 |
| 6.27 | 0.94 |
| 5.90 | 0.68 |
| 5.75 | 0.54 |
| 5.46 | 0.49 |

TABLE 3

| d(Å) | I/I₀ |
|---|---|
| 16.02 | 0.77 |
| 10.01 | 0.62 |
| 8.94 | 0.63 |
| 7.89 | 0.56 |
| 6.84 | 0.73 |
| 6.00 | 0.89 |
| 5.87 | 1.00 |
| 5.81 | 0.93 |
| 5.37 | 0.63 |

TABLE 3a

| d(Å) | I/I₀ |
|---|---|
| 16.02 | 0.77 |
| 10.01 | 0.62 |
| 8.94 | 0.63 |
| 7.89 | 0.56 |
| 6.84 | 0.73 |
| 6.65 | 0.46 |
| 6.00 | 0.89 |
| 5.87 | 1.00 |
| 5.81 | 0.93 |
| 5.37 | 0.63 |
| 5.14 | 0.46 |
| 4.93 | 0.44 |
| 4.57 | 0.40 |
| 4.33 | 0.39 |
| 4.24 | 0.34 |
| 4.18 | 0.29 |
| 3.64 | 0.25 |
| 3.60 | 0.28 |

A compound of formula I in stable and anhydrous form according to the present invention may be non-hygroscopic, e.g. it may keep a water content below 1% even after several hours, e.g. 24 hours, under normal, e.g. normal air humidity, environmental conditions. This is surprising because known compounds of formula I may not keep a water content below 1% under normal e.g. air humidity, environmental conditions but may take up water from the environment within short time, e.g. some hours resulting in a water content which is above 1%.

The X-ray powder diffraction pattern of a compound of formula I in stable anhydrous form is different from the X-ray powder diffraction pattern of a known compound in unstable, e.g. hygroscopic anhydrous form which is shown in Table 4 below:

TABLE 4

| d(Å) | I/I₀ |
|---|---|
| 15.13 | 0.27 |
| 12.96 | 0.21 |
| 9.92 | 0.47 |
| 8.78 | 0.46 |
| 7.61 | 1.00 |
| 6.93 | 0.34 |
| 6.76 | 0.39 |
| 6.39 | 0.38 |
| 6.01 | 0.65 |
| 5.71 | 0.34 |
| 5.08 | 0.56 |
| 4.88 | 0.32 |
| 4.58 | 0.28 |
| 4.35 | 0.23 |

In Tables 1, 1a, 2, 2a, 3, 3a and 4 d denotes the interplanar spacing, I/I₀ denotes the relative intensity and Å denotes Angstroem.

In case of using aromatic solvent and production of a compound of formula I in the form of a hemihydrate, a mixture of erythromycin A oxime, water and aromatic solvent may be stirred, e.g. in order to achieve a uniform mixture. Erythromycin A oxime in the form of a hemihydrate may precipitate and may be isolated, e.g. as conventional, e.g. by filtration, centrifugation. An, e.g. isolated, composition of erythromycin A oxime in the form of a hemihydrate containing aromatic solvent, e.g. up to ca. 30% (w/w), such as ca. 1 to 15% (w/w) is novel.

An isolated, composition of erythromycin A oxime hemihydrate and aromatic solvent, may be dried, e.g. under fast and mild conditions, e.g. at temperatures from 50° C. and above, e.g. in vacuo, for example at temperatures in vacuo of 50° C. to 90° C., to give erythromycin A oxime, e.g. a compound of formula I, in the form of a hemihydrate in a stable, non-hygroscopic form, e.g. having a high content of, e.g. desired E-isomer and a low content of, e.g. undesired Z-isomer. Dried erythromycin A oxime in the form of a hemihydrate obtainable according to the present invention may contain e.g. traces, of, e.g. residual, aromatic solvent, such as 0.01%, e.g. 0.05% up to ca. 1%, e.g. about 0.1% (w/w).

In another aspect the present invention provides an, e.g. isolated, composition containing aromatic solvent e.g., in an amount of 0.01% to 30% w/w, and erythromycin A oxime, e.g. of formula I, in the form of a herihydrate.

The advantage of a compound of formula I in the form of a solvate with non-halogenated solvent and processes for its production according to the present invention may be as follows:

Yields may be high. A compound of formula I in stable and anhydrous form may be obtained from a compound of formula I in form of a solvate in a yield (assay) higher than 96%, e.g. up to 99% and more. A compound of formula I in stable and anhydrous form may be obtained from a compound of formula I in salt form in an overall yield higher than 88%, e.g. up to 90% and more.

Non-halogenated organic solvents are used. One single organic solvent may be used.

A compound of formula I in form of a solvate with non-halogenated solvent and in stable and anhydrous form may be obtained in high purity, e.g. low Z-isomer content.

A compound of formula I in form of a solvate with non-halogenated solvent may be stable and non-hygroscopic.

A compound of formula I in stable, anhydrous form has the following advantages:

a) It may have a water content below 1%, even below 0.3%, such as 0.2% to 0.9% e.g. 0.3 to 0.6%. This may be important in reactions where the presence of water should be avoided.

b) It may be stable, e.g. non hygroscopic, keeping its water content below 1% for a long time under normal environmental conditions.

c) It may be obtained in high purity, e.g. the content of the Z-isomer may be very low, e.g. such as below 2%.

A process according to the present invention using aromatic solvent and a compound of formula I in the form of a hemihydrate may have the following advantages:

A compound of formula I in the form of a hemihydrate may be stable and non-hygroscopic, e.g. keeping a water content below 2% even after several hours, e.g. 24 hours, under normal, e.g. normal air humidity, environmental conditions Yields may be high; e.g. erythromycin A oxime in the form of a hemihyydrate may be obtained from a compound of formula I in salt, e.g. hydrochloride, form in a yield higher than 85%, e.g. higher than 90%, such as even 93%; and more The production process is simple and do not require time-consuming extraction and concentrating steps A compound of formula I in the form of a hemihydrate may be obtained in high purity, e.g., having a low content of undesired Z-isomer, e.g. lower than 2%; and having a high content of the E-isomer, e.g. higher than 95%, e.g. even higher than 97%

The processes and a compound of the present invention may be used on industrial scale.

A compound of the present invention may be used as such, e.g. as an intermediate in the production of, e.g. semi-synthetic, e.g. pharmaceutically active, macrolides such as of the erythromycin, e.g. A type, such as roxithromycin, dirithromycin, clarithromycin and azithromycin, preferably roxythromycin, clarithromycin, or azithromycin, e.g. via further intermediate(s).

In another aspect the present invention provides a compound of formula I in stable, anhydrous form, or in the form of a solvate with non-halogenated solvent, or in the form of a hemihydrate for use in the production of a macrolide from the erythromycin type; and in another aspect the use of a compound of formula I in stable, anhydrous form, or in the form of a solvate with non-halogenated solvent, or in the form of a hemihydrate in the production of a macrolide of the erythromycin type; and in another aspect a process for the production of a macrolide from the erythromycin type comprising converting a compound of formula I in stable, anhydrous form, or in the form of a solvate with non-halogenated solvent, or in the form of a hemihydrate into a macrolide from the erythromycin, e.g. A, type.

Roxythromycin may be obtained from erythromycin A oxime e.g. by alkylation of the hydroxy group of the oxime, e.g. by a process as conventional, e.g. according to a method as described in ES 2,024,371 with a compound according to the present invention as a starting compound, instead of, e.g. a known unstable, such as hygroscopic compound of formula I.

In a further aspect the present invention provides a process for the production of roxythromycin comprising alkylating the hydroxy group of the oxime group of a compound of formula I in stable, anhydrous form, or in the form of a solvate with non-halogenated solvent, or in the form of a hemihydrate.

Clarithromycin may be obtained from erythromycin A oxime e.g. by methylating the hydroxy group in position 6 of a compound of formula I and deoximation, e.g. by a process as conventional.

In a further aspect the present invention provides a process for the production of clarithromycin comprising the steps (i) deoximating and (ii) alkylating the hydroxy group in position 6 of a compound of formula I, characterized in that a compound of formula I in stable, anhydrous form, or in the form of a solvate with non-halogenated solvent, or in the form of a hemihydrate is used, e.g. as an intermediate, e.g. as a starting material, e.g. in deoximation and/or alkylation of the hydroxy group in position 6.

Azithromycin may be obtained from a compound of formula I via a Beckmann rearrangement and, e.g. after reduction, a 9-deoxo-9a-aza-9a-homoerythromycin A obtained may be methylated in the 9a-aza position, e.g. by a process as conventional.

In a further aspect the present invention provides a process for the production of azithromycin wherein a compound of formula I is rearranged via a Beckmann rearrangement and the 9-deoxo-9a-aza-9a-homo-erythromycin A obtained after reduction is methylated in the 9a-aza position, characterized in that a compound of formula I in stable, anhydrous form, or in the form of a solvate with non-halogenated solvent, or in the form of a hemihydrate is used, e.g. as an intermediate, e.g. as a starting material, e.g. in a Beckamnn rearrangement reaction.

The use of erythromycin A oxime in the form in stable, anhydrous form, or in the form of a solvate with non-halogenated solvent, or in the form of a hemihydrate as a starting material in the production of a macrolide according to the present invention may have the following advantages:

The starting material may be stable

The starting material may be pure, e.g. containing less than 2% of the Z-isomer

The starting material may contain only one single, e.g. residual organic solvent The starting material may be produced on industrial scale in an economical and ecological process.

The following non limitative examples illustrate the invention. All temperatures are given in degree Celsius and are uncorrected. The content of erythromycin A oxime in the starting material and in a solvate of erythromycin A oxime with non-halogenated solvent and in erythromycin A oxime in the form of a hemihydrate (assay) is determined by liquid chromatography (HPLC). The solvent content in the solvates of erythromycin A oxime with non-halogenated solvent and the aromatic solvent content in a compound of formula I in stable form and in the form of a hemihydrate is determined by (head space) gas chromatography.

EXAMPLES 1 AND 2

(Differences of Example 2 in Respect with Example 1 are Indicated in Brackets)

20 g (10 g) of erythromycin A oxime in the form of a hydrochloride with an erythromycin A oxime content based on the free base of 77.0% (82.6%) are suspended in a mixture of 110 ml (50 ml) of water and 125 ml of toluene (120 ml of xylene). The mixture is warmed to 30° to 40° (25° to 30°) and the pH of the mixture is adjusted to 9.0 to 9.5 by the addition of 25% w/w aqueous ammonia. The suspension obtained is stirred at 40° within 2 hours (30 minutes) and the pH is re-adjusted to 9.0 to 9.5. Erythromycin A oxime in the form of a hemihydrate precipitates, is filtrated off, washed with water and toluene (xylene) and dried at 65°. 14.58 g (7.83 g), which is 93% (92%) of theory, of erythromycin A oxime in the form of a hemihydrate are obtained. HPLC content (assay): 98.5% (97.9%) on anhydrous basis. Water content—Karl Fischer: 1.6% (1.6%). Water content after 3 days at normal environmental conditions: 1.6% (1.6%) Thermogravimetric analysis: loss weight between 100° and 200°: 1.15%

EXAMPLES 3 TO 6

General Procedure

A) Erythromvcin A Oxime in Form of a Solvate with a Solvent as Indicated Under "Solvent" in Table 4 Below An amount of erythromycin A oxime in form of a hydrochloride in gram as indicated in TABLE 4 below under "Start (g)" (erythromycin A oxime content based on the free base as indicated under "E-A %" in TABLE 4 below) is suspended in a mixture of an amount of water in ml as indicated under "Water" in TABLE 4 below and an amount as indicated under "S (ml)" in ml in TABLE 4 below of a solvent as indicated under "Solvent" in TABLE 4 below at a temperature in degree Celsius as indicated under "T° C." in TABLE 4 below. The pH is adjusted to pH 9.3 to 9.5 by addition of 25% (w/w) aqueous ammonia. The mixture is stirred and a two phase system is obtained. The phases are separated and the organic phase is dried over anhydrous sodium sulphate. The solid is filtrated off and the filtrate is concentrated under reduced pressure. Solid erythromycin A oxime in form of a solvate with a solvent as indicated under "Solvent" in TABLE 4 below precipitates, is filtrated off and dried overnight in vacuo at a temperature in degree Celsius as indicated under "DT° C." in TABLE 4 below, and obtained in a yield in gram as indicated under "Yield" in TABLE 4 below, having a solvent content of a solvent as indicated under "Solvent" in TABLE 4 below in % as indicated under "S-cont" in TABLE 5 below. The molar ratio of solvent as indicated under "Solvent" in TABLE 4 below and erythromycin A oxime is about 1:1.

B) Erythromycin A Oxime in Stable and Anhydrous Form

Erythromycin A oxime in form of a solvate with a solvent as indicated under "Solvent" in TABLE 4 below as obtained according to step A) is dried at a temperature as indicated under "DDT° C." in TABLE 5 below for a time (circa) in hours as indicated under "Hours" in TABLE 5 below. Erythromycin A oxime in stable and anhydrous form is obtained in a yield in gram as indicated under "DYield" in TABLE 5 below, having a content of erythromycin A oxime in % (assay) as indicated under "Assay" in TABLE 4 below and a water content in % as indicated under "Wat %" in TABLE 5 below. The overall yield based on erythromycin A oxime hydrocloride used as a starting material in % is as indicated under "OverY" in TABLE 5 below. The X-ray powder diffraction pattern is as given in that TABLE above which is indicated under "TNo." in TABLE 4 below.

TABLE 4

| Example | Solvent | Start (g) | E-A % | Water | S (ml) | T ° C. | DT ° C. | Yield |
|---|---|---|---|---|---|---|---|---|
| 3 | isopropyl acetate | 63.2 | 80.9 | 380 | 560 | 20 | 25–30 | 52.9 |
| 4 | n-butyl acetate | 50.0 | 84.4 | 300 | 575 | 25 | 35–40 | 41.2 |
| 5 | methyl-isobutyl ketone | 62.0 | 83.9 | 380 | 430 | 20 | 35–40 | 45.6 |
| 6 | ethyl acetate | 130 | 77.1 | 400 | 920 | room | — | 101.5 |

TABLE 5

| Example | S-cont | DDT ° C. | Hours | DYield | Assay | Wat % | OverY | TNo. |
|---|---|---|---|---|---|---|---|---|
| 3 | 11.0 | 70 | 8 | 46.6 | 98.4 | 0.4 | 89.2 | 1 + 1a |
| 4 | 10.8 | 70 | 8 | 36.3 | 97.1 | 0.5 | 83.2 | 2 + 2a |
| 5 | 10.4 | 60 | 8 | 40.4 | 95.6 | 0.5 | 74.3 | 3 + 3a |
| 6 | 9.0 | 60–65 | 9 | 93.11 | 96.7 | 0.6 | 88.5 | 1 + 1a |

What is claimed is:

1. Erythromycin A oxime of formula

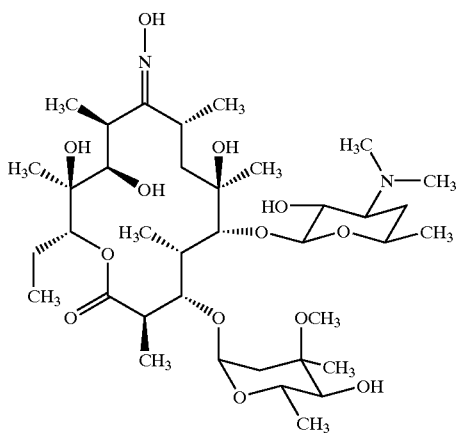

I in the form of a hemihydrate.

* * * * *